United States Patent
Barack

(10) Patent No.: US 10,915,198 B2
(45) Date of Patent: Feb. 9, 2021

(54) BREAST PUMP OR OTHER MEDICAL DEVICES WITH DYNAMICALLY ADAPTIVE PUMP CONFIGURATION PROVIDING ERROR DETECTION AND DISTINCTIVE SUCTION PROFILE

(71) Applicant: CLINICARE LTD., Raanana (IL)

(72) Inventor: Doron Barack, Ra'anana (IL)

(73) Assignee: CLINICARE LTD., Raanana (IL)

( * ) Notice: Subject to any disclaimer, the term of this patent is extended or adjusted under 35 U.S.C. 154(b) by 576 days.

(21) Appl. No.: 15/535,710

(22) PCT Filed: Jun. 1, 2017

(86) PCT No.: PCT/IL2017/050612
§ 371 (c)(1),
(2) Date: Jun. 14, 2017

(87) PCT Pub. No.: WO2017/208243
PCT Pub. Date: Dec. 7, 2017

(65) Prior Publication Data
US 2018/0110906 A1    Apr. 26, 2018

Related U.S. Application Data

(60) Provisional application No. 62/343,164, filed on May 31, 2016, provisional application No. 62/343,170, (Continued)

(51) Int. Cl.
*G06F 3/041* (2006.01)
*A61M 1/00* (2006.01)
(Continued)

(52) U.S. Cl.
CPC ......... *G06F 3/0416* (2013.01); *A61M 1/0035* (2014.02); *A61M 1/0066* (2013.01);
(Continued)

(58) Field of Classification Search
CPC ........ A61M 1/06; A61M 1/062; A61M 1/064; A61M 1/066; A61M 1/068
See application file for complete search history.

(56) References Cited

U.S. PATENT DOCUMENTS 5,348,076 A * 9/1994 Asakawa ........... H05K 7/20281
165/104.33
5,954,690 A * 9/1999 Larsson ............... A61M 1/0068
604/152

(Continued)

*Primary Examiner* — Nathan R Price
*Assistant Examiner* — Dung T Ulsh
(74) *Attorney, Agent, or Firm* — Mark M. Friedman

(57) ABSTRACT

A pump unit (10) includes a number of pumps (14) each having a port in fluid connection to a combined port (12) of the pump unit. A processing system (16) is connected to each of the pumps (14) for independent actuation of each pump. A user interface (22) allows user actuation of the pump unit according to one or more mode of operation, requiring various different levels of suction or pressure. The processing system (16) determines what number of pumps (14) is required, and selectively actuates pumps in order to generate the required suction or pressure. Particularly preferred applications include breast pumps. Additional aspects of the invention relate to a cyclic pulsed suction profile generated by the device, implementations that detect when a milk extraction set is not properly deployed, and configurations which allow a touch screen to be used as a power-on switch for the device.

22 Claims, 7 Drawing Sheets

Related U.S. Application Data filed on May 31, 2016, provisional application No. 62/352,032, filed on Jun. 20, 2016, provisional application No. 62/353,049, filed on Jun. 22, 2016.

(51) Int. Cl.

| | | |
|---|---|---|
| *A61M 1/06* | (2006.01) | |
| *F04B 49/00* | (2006.01) | |
| *F04B 49/06* | (2006.01) | |
| *F04B 23/06* | (2006.01) | |
| *F04B 23/04* | (2006.01) | |
| *F04B 43/00* | (2006.01) | |
| *F04B 45/047* | (2006.01) | |
| *F04B 35/04* | (2006.01) | |
| *F04B 49/08* | (2006.01) | |
| *G06F 3/045* | (2006.01) | |
| *G16H 40/63* | (2018.01) | |

(52) U.S. Cl.
CPC .............. *A61M 1/06* (2013.01); *A61M 1/066* (2014.02); *F04B 23/04* (2013.01); *F04B 23/06* (2013.01); *F04B 35/04* (2013.01); *F04B 43/00* (2013.01); *F04B 45/047* (2013.01); *F04B 49/007* (2013.01); *F04B 49/06* (2013.01); *F04B 49/08* (2013.01); *A61M 2205/13* (2013.01); *A61M 2205/17* (2013.01); *A61M 2205/18* (2013.01); *A61M 2205/3331* (2013.01); *A61M 2205/3337* (2013.01); *A61M 2205/3344* (2013.01); *A61M 2205/42* (2013.01); *A61M 2205/50* (2013.01); *A61M 2205/505* (2013.01); *A61M 2205/581* (2013.01); *A61M 2205/583* (2013.01); *A61M 2205/70* (2013.01); *A61M 2205/8206* (2013.01); *G06F 3/045* (2013.01); *G16H 40/63* (2018.01)

(56) References Cited

U.S. PATENT DOCUMENTS

| | | | |
|---|---|---|---|
| 2003/0069536 A1 | 4/2003 | Greter et al. | |
| 2007/0257890 A1* | 11/2007 | Hotelling | G06F 3/044 |
| | | | 345/173 |
| 2008/0009815 A1* | 1/2008 | Grabenkort | A61M 1/0068 |
| | | | 604/346 |
| 2008/0177224 A1 | 7/2008 | Kelly et al. | |
| 2009/0160819 A1 | 6/2009 | Sasaki et al. | |
| 2010/0042074 A1* | 2/2010 | Weston | A61M 1/0068 |
| | | | 604/543 |
| 2010/0152652 A1* | 6/2010 | Weston | A61M 1/0072 |
| | | | 604/74 |
| 2011/0004154 A1* | 1/2011 | Van Schijndel | A61M 1/06 |
| | | | 604/74 |
| 2011/0056192 A1 | 3/2011 | Weber et al. | |
| 2011/0071466 A1* | 3/2011 | Silver | A61M 1/0072 |
| | | | 604/74 |
| 2011/0270163 A1* | 11/2011 | Britto | A61M 1/06 |
| | | | 604/74 |
| 2013/0241689 A1 | 9/2013 | Nakajima et al. | |
| 2013/0267933 A1* | 10/2013 | Felber | A61M 1/06 |
| | | | 604/514 |
| 2014/0031744 A1* | 1/2014 | Chen | A61M 1/06 |
| | | | 604/74 |
| 2014/0034162 A1* | 2/2014 | Mackey | F04B 23/021 |
| | | | 137/565.29 |
| 2014/0268628 A1* | 9/2014 | Mann | G08C 17/00 |
| | | | 362/23.1 |
| 2014/0378946 A1* | 12/2014 | Thompson | A61M 1/062 |
| | | | 604/514 |
| 2016/0282990 A1* | 9/2016 | Kimura | G02F 1/13338 |
| 2016/0287767 A1* | 10/2016 | Simmons | A61M 1/062 |
| 2016/0325031 A1* | 11/2016 | Miller | A61M 1/062 |
| 2017/0152849 A1* | 6/2017 | Turczak | F04B 17/03 |
| 2018/0003170 A1* | 1/2018 | Ruger | B05B 9/0406 |

\* cited by examiner

BREAST PUMP OR OTHER MEDICAL DEVICES WITH DYNAMICALLY ADAPTIVE PUMP CONFIGURATION PROVIDING ERROR DETECTION AND DISTINCTIVE SUCTION PROFILE

FIELD AND BACKGROUND OF THE INVENTION

The present invention applies to pump units for medical devices and other consumer products to produce suction or pressure, and most preferably to breast pumps used to apply suction to a complementary pumping kit including tubing, a breast-shield and a bottle, for the extraction of a mother's breast milk. In particular, the invention concerns a pump with a dynamically adaptive pump configuration employing an array of pumps, and which preferably provides error detection and/or a distinctive suction profile.

Conventional medical pump devices, and particularly breast pumps, usually employ a single motor/pump that creates the required pressure (vacuum and/or positive pressure), typically pulsed at a required rate (number of cycles per minute). The motor must be chosen according to the highest vacuum conditions for which the device is designed, and must be able to operate continuously for the maximum period of time for which the device is designed to operate. This often results in use of motors capable of performance way beyond the everyday conditions under which they are normally used, and which are therefore relatively expensive, over-powered, overly noisy and unnecessarily energetically inefficient when operating under typical usage conditions. Additionally, when operating a high-power pump at a small proportion of its capacity, it is often difficult to adjust the pump output accurately and maintain a desired vacuum level.

SUMMARY OF THE INVENTION

The present invention includes a number of different aspects, including a breast pump with a dynamically adaptive pump configuration and/or which provides error detection and/or a distinctive suction profile.

According to the teachings of an embodiment of the present invention there is provided, a pump unit comprising: (a) a plurality of air pumps, each of the pumps having a port, the ports of all of the pumps being in fluid connection to a combined port of the pump unit; (b) a processing system comprising at least one processor, the processing system being connected to each of the pumps for independent actuation of each of the pumps; and (c) a user interface associated with the processing system for user actuation of the pump unit according to any of a plurality of required levels of suction or pressure, wherein the processing system is configured to: (i) determine a number of the pumps that is required to generate the required level of suction or pressure; and (ii) to selectively actuate the number of the pumps in order to generate the required level of suction or pressure.

According to a further feature of an embodiment of the present invention, when the number of the pumps is less than all of the pumps, the processing system is configured to vary which of the pumps is actuated.

According to a further feature of an embodiment of the present invention, the processing system is further configured to actuate the plurality of pumps to generate a cyclic time-varying pressure profile, the processing system actuating a first number of the pumps during a first portion of each cycle of the pressure profile and a second number of pumps, different from the first number, during a second portion of each cycle of the pressure profile.

According to a further feature of an embodiment of the present invention, each of the pumps is provided with an electrically controlled cut-off valve, and wherein the processing system is further configured to actuate the electrically controlled cut-off valve to block flow to the combined port through at least one of the pumps that is not currently actuated.

According to a further feature of an embodiment of the present invention, the processing system is further configured to: (a) perform a self-test to identify any defective pump among the plurality of pumps; and (b) to selectively actuate the number of the pumps without use of the defective pump.

According to a further feature of an embodiment of the present invention, each of the pumps is a diaphragm pump.

According to a further feature of an embodiment of the present invention, each of the pumps is a modular unit configured to be individually replaceable with a similar pump without use of tools.

According to a further feature of an embodiment of the present invention, there is also provided a pressure sensor, associated with the processing system, and deployed to measure a fluid pressure at the combined port.

According to a further feature of an embodiment of the present invention, there is also provided an electrically actuatable vent valve, connected so as to be controlled by the processing system, and deployed to selectively allow rapid release of suction or pressure at the combined port.

According to a further feature of an embodiment of the present invention, the processing system is further configured to actuate the plurality of pumps to generate a cyclic time-varying suction profile, each cycle of the suction profile including: (a) a suction rise time during which the suction increases to a target value; (b) a suction hold time during which the suction is maintained substantially at the target value; and (c) a suction release time during which the suction is released to fall to a base value, wherein the suction hold time is at least 15% of a total cycle time.

According to a further feature of an embodiment of the present invention, the processing system is further configured to process data derived from at least one sensor to determine during operation of the pump unit whether the pump is operating in a normal state or in an unsealed state in which the pump fails to achieve effective suction or pressure, and wherein the processing system is further configured to perform a corrective action if the unsealed state persists for a given time period of operation of the pump unit.

According to a further feature of an embodiment of the present invention, the user interface comprises a resistive touch panel having a transparent first conductive layer and a transparent second conductive layer arranged in facing relation to the first conductive layer so as to be selectively brought into electrical contact with the first conductive layer on application of mechanical pressure to the resistive touch panel, a display screen underlying the touch panel, a display controller for driving the display screen, and touch panel circuitry for driving electrodes associated with at least one of the first and second conductive layers so as to generate signals sufficient to determine a panel location at which mechanical pressure is applied, wherein the pump unit is configured to assume an off configuration in which the display controller is powered-down and the processing system is in a sleep mode with an open-circuit voltage differential applied between the first and second conductive layers, the touch panel serving as a power-on switch effective to initiate awakening of the processing system and powering-up of the display controller when mechanical pressure is applied to the resistive touch panel.

There is also provided according to the teachings of an embodiment of the present invention, a breast pump unit comprising: (a) a suction pump subsystem comprising at least one suction pump in fluid connection with a suction port; and (b) a processing system comprising at least one processor, the processing system being connected to the suction pump subsystem and configured to actuate the suction pump subsystem to generate a cyclic time-varying suction profile, each cycle of the suction profile including: (i) a suction rise time during which the suction increases to a target value; (ii) a suction hold time during which the suction is maintained substantially at the target value; and (iii) a suction release time during which the suction is released to fall to a base value, wherein the suction hold time is at least 15% of a total cycle time.

According to a further feature of an embodiment of the present invention, the suction rise time and the suction hold time together make up a total pulse time within each cycle, and wherein the suction hold time is at least 40% of the total pulse time and at least a 20% of a total cycle time.

There is also provided according to the teachings of an embodiment of the present invention, a breast pump unit comprising: (a) a suction pump subsystem comprising at least one suction pump in fluid connection with a suction port; and (b) a processing system comprising at least one processor, the processing system being connected to the suction pump subsystem and configured to actuate the suction pump subsystem to generate suction within a breast shield set connected to the suction port, wherein the processing system is further configured to process data derived from at least one sensor to determine during operation of the breast pump unit whether the breast pump unit is operating in a normal suction state or in an unsealed state in which the suction pump fails to achieve effective suction, and wherein the processing system is further configured to perform a corrective action if the unsealed state persists for a given time period of operation of the breast pump unit.

According to a further feature of an embodiment of the present invention, the corrective action includes generating a visual and/or audio alert.

According to a further feature of an embodiment of the present invention, the corrective action includes discontinuing operation of the pump unit.

There is also provided according to the teachings of an embodiment of the present invention, a pump unit comprising: (a) a pump subsystem comprising at least one pump in fluid connection with a port; (b) a processing system comprising at least one processor, the processing system being connected to the pump subsystem and configured to actuate the pump subsystem to generate suction or pressure at the port; and (c) a user interface associated with the processing system for user actuation of the pump unit, wherein the user interface comprises a resistive touch panel having a transparent first conductive layer and a transparent second conductive layer arranged in facing relation to the first conductive layer so as to be selectively brought into electrical contact with the first conductive layer on application of mechanical pressure to the resistive touch panel, a display screen underlying the touch panel, a display controller for driving the display screen, and touch panel circuitry for driving electrodes associated with at least one of the first and second conductive layers so as to generate signals sufficient to determine a panel location at which mechanical pressure is applied, wherein the pump unit is configured to assume an off configuration in which the display controller is powered-down and the processing system is in a sleep mode with an open-circuit voltage differential applied between the first and second conductive layers, the touch panel serving as a power-on switch effective to initiate awakening of the processing system and powering-up of the display controller when mechanical pressure is applied to the resistive touch panel.

According to a further feature of an embodiment of the present invention, the touch panel circuitry is implemented as part of the processing system.

According to a further feature of an embodiment of the present invention, there is also provided delay circuitry associated with the resistive touch panel and configured such that the touch panel effects power-up of the processing system only when mechanical pressure is applied to the touch panel for a period in excess of a defined delay.

According to a further feature of an embodiment of the present invention, the pump unit is a breast pump configured to apply suction to a breast shield set connected to the combined port.

BRIEF DESCRIPTION OF THE DRAWINGS

The invention, is herein described, by way of example only, with reference to the accompanying drawings, wherein.

DESCRIPTION OF THE PREFERRED EMBODIMENTS

Figure 1:
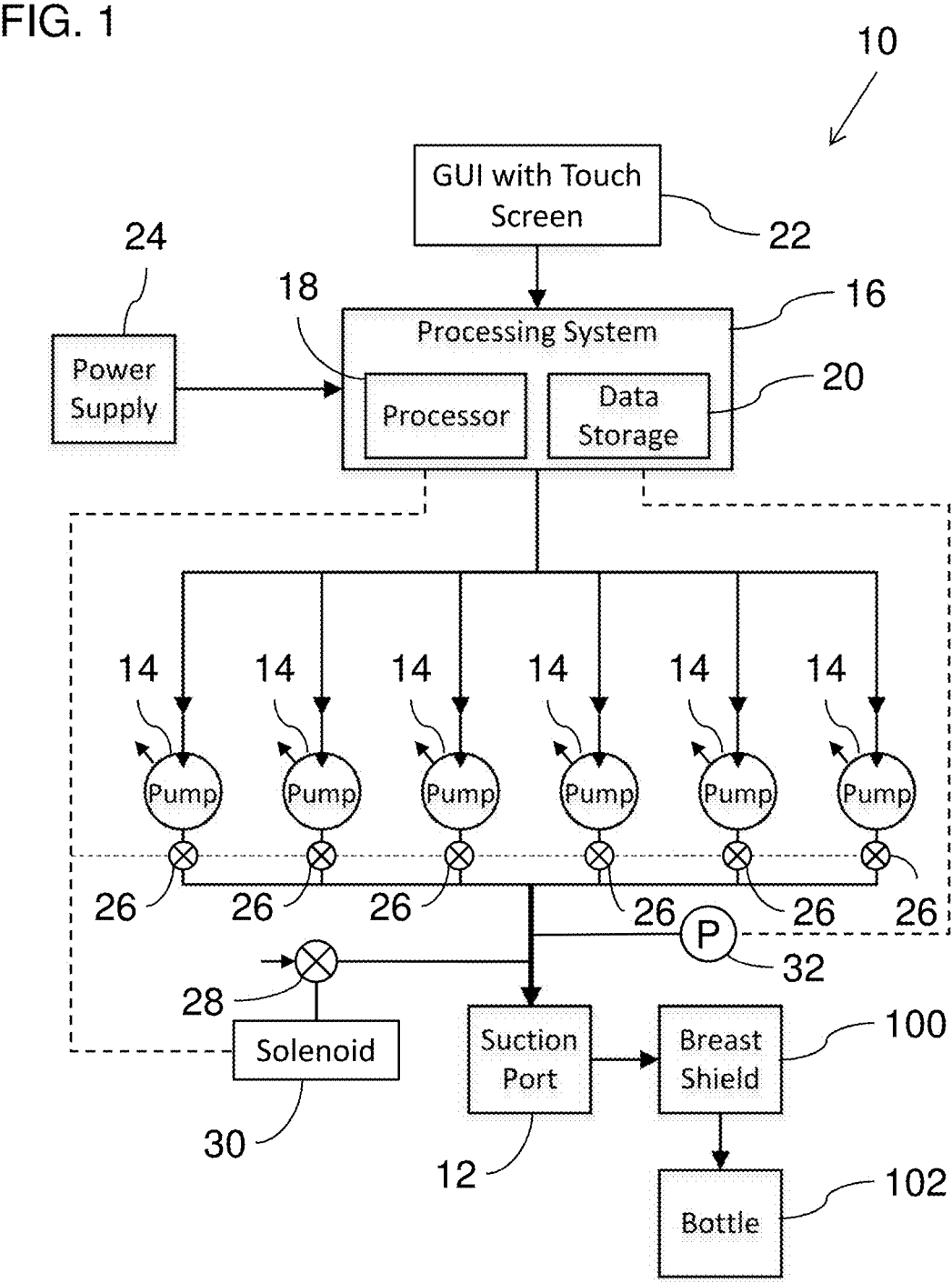
FIG. 1 is a schematic block diagram of a pump unit, constructed and operative according to the teachings of an embodiment of the present invention.

The present invention is a suction pump unit, and corresponding methods of operating a suction pump.

The principles and operation of pump units according to the present invention may be better understood with reference to the drawings and the accompanying description.

By way of introduction, the present invention relates to a pump unit for consumer products, and especially medical applications, broadly defined as anything related to the wellbeing, convenience or health of the user. The invention will be illustrated primarily in the context of a particularly preferred application as a breast pump used to apply suction to a complementary pumping kit including tubing, a breast-shield and a bottle, for the extraction of a mother's breast milk. However, it should be noted that the present invention is not limited to applications as a breast pump, and various features of the invention described herein are equally applicable to various additional medical and other pump applications, as will be clear to a person having ordinary skill in the art.

A particularly preferred implementation of the suction pump unit of the present invention includes a number of novel features, each of which can be utilized to advantage independently and corresponds to a distinct aspect of the present invention. Specifically, a first aspect of the present invention, described particularly with reference to FIGS. 1 and 2, relates to suction pump configuration which includes a plurality of small pumps which are selectively actuated by a control system so as to work independently or together, according to the required level of suction, to achieve a desired pumping effect. A second aspect of the present invention, described particularly with reference to FIGS. 3B and 4, relates to implementation of a suction pulse form which is believed to be particularly advantageous for extraction of breast milk. A third aspect of the present invention relates to sensing and handling of various error states regarding connection of a pumping kit to the suction pump. A fourth aspect of the present invention, described particularly with reference to FIGS. 5-7, relates to an implementation of the suction pump in which a resistive touch screen serves as an ON switch for powering on the device without requiring a separate power button. These various aspects of the invention can be combined synergistically in any desired combination.

In the following description, the terms "suction pump", "pump unit" and the like are generally used interchangeably, and include, but are not limited to, "breast pumps", except where stated otherwise. The terms "suction" and "vacuum" are used interchangeably, and refer to states of partial vacuum, where the term "higher" generally refers to an increased level of vacuum, i.e., reduced pressure. Thus, suction pulse forms are illustrated (FIGS. 3A and 3B) with suction (negative pressure) in the positive Y coordinate. Alternative applications of the invention relate to devices which generate pressure (i.e., elevated or "positive" pressure). The present invention relates particularly to applications that operate at levels of suction or pressure which can be achieved using low-cost pumps, and typically, for suction applications not needing to reach vacuum levels greater than 1 kPa, and positive pressure applications not needing to reach pressures of more than about 500 kPa. For many applications, suction levels of about 50 kPa (about half an atmosphere of suction) or pressure levels of up to about 200 kPa (about one atmosphere of positive pressure) are sufficient.

The terms "pump unit" and "pump device" are used herein interchangeably, and do not imply any limitations as to the form factor of the device, or the number of separate housings. Part or all of a control system may, for example, be housed separately from the pumps, with wired or wireless communication between the components.

Where reference is made to a component being "powered-off", this refers to interruption of electrical power supply to that component. Where reference is made to a component being in a "sleep" state, this refers to switching of the component to a high-impedance state in which power consumption is greatly reduced, and which can be made to "awaken" to a normal state of operation by application of a predefined voltage trigger to one of the component's inputs.

Dynamically Allocated Pumping Resources

Referring now to the drawings, FIG. 1 illustrates schematically a breast pump, generally designated 10, constructed an operative according to the teachings of the present invention, used to apply suction from a suction port 12 via tubing to a breast-shield 100 connected to a bottle 102, for the extraction of a mother's breast milk.

In general terms, according to the first aspect of the present invention, pump unit 10 includes a plurality of suction pumps 14, preferably at least three, and in most cases between and 8 suction pumps 14, each having a suction port in fluid connection to the combined suction port 12 of pump unit 10. A processing system 16, including at least one processor 18 and typically a data storage device 20, is connected to each of pumps 14 for independent actuation of each pump. A user interface 22, associated with processing system 16, allows user actuation of the pump unit according to one or more mode of operation, which require a plurality of required levels of suction, typically implemented in a cyclically pulsed suction profile as will be discussed further below.

It is a particular feature of this aspect of the present invention that processing system 16 is configured to determine what number of pumps 14 is required to generate a currently required level of suction, and to selectively actuate that number of pumps in order to generate the required level of suction.

Processing system 16 thus preferably serves as a breast pump control system, implementing a control logic which selectively applies a voltage to one or more of pumps 14, which are preferably relatively low-powered pumps, referred to herein as "micro-vacuum pumps", so as to provide a desired level of vacuum to the pump vacuum port, for applying that vacuum to a milk-extraction kit. When the required vacuum is relatively low, the logic of the breast pump may use only one micro-vacuum pump to create the required vacuum and cycle rate.

The multiple pumps may be considered a Redundant Array of Low Power Pumps (RALPP), to be dynamically allocated according to the demands required from the pump unit at any given time, together with various resource allocation algorithms, as will be clear to a person having ordinary skill in the art on the basis of the following description. Thus, by using selective switching of multiple small pumps, the system of the present invention may provide one or more of the following benefits:

1. Adaptive power consumption—Power consumption depends on the number of the micro-pumps that are needed to create the required vacuum level: Less vacuum requires actuation of fewer micro vacuum pumps operating together, resulting in less energy wastage.
2. Noise optimization—Using adaptive number of micro vacuum pumps in the breast pump reduces also the noise produced by the breast pump which correlates to the number of micro vacuum pumps used for a pumping session.
3. Redundancy—Furthermore, when using more micro vacuum pumps than are required for typical pumping rates or vacuum levels, the system is provided with inherent redundancy, thereby allowing the breast pump to continue operating properly even if a subset of the micro vacuum pumps develop faults and are inoperative.
4. Prolonging overall life span of the pump—The above redundancy also enables rotation between the different pumps, alternating which pumps are used whenever only a subset are required, thereby reducing the number of hours each pump is operated and extending the total life span of the breast pump.
5. Low cost modular design—The use of multiple low-cost pumps also facilitates a modular design in which a faulty pump can readily be swapped-out and replaced for a small proportion of the cost of an entire replacement unit. This contrasts to conventional single-pump devices where the cost of replacing the pump would be a major proportion of the cost of an entire replacement unit.

The ability to provide high reliability and increased versatility using low-cost pumps through providing redundancy and suitable control electronics can readily be adapted to a wide range of low-vacuum or low-pressure pumping applications, ranging from our primary example of a breast pump, through other medical devices (e.g., "suction" equipment, pressure for surgical applications, nebulizers etc.) to other consumer products as diverse as compressors for heat pumps (air conditioning or refrigerators) and fuel pumps for vehicles. The necessary adaptations for each application will be readily understood by a person ordinarily skilled in the art on the basis of the description herein.

The attached FIG. 1 illustrates a typical example of a pump unit according to an embodiment of the present invention employing 6 micro vacuum pumps 14, controlled by processing system 16. Settings for the pump unit may be provided via graphic user interface (GUI) 22, which may include a display and various buttons, but is most preferably implemented as a touch-screen. The processing system selectively applies power from a power source 24, which may be a battery source or an external power source, to activate a selected subset of pumps 14 according to the required suction level and pulse form and frequency. For example, if the breast pump needs only two micro vacuum pumps per pumping session to achieve the currently set suction level, logic of the breast pump preferably employs alternating selection of two pumps, selecting a different pair for each session, and thus prolonging the overall life span of the breast pump. Thus, if the pumps are identified by the system as P1-P6, pumping may start with pumps P1 and P2, while P3-P6 remain inactive, thereby keeping power consumption and noise to the minimum necessary. For the next session, pumps P3 and P4 may be used, and for a subsequent session, P5 and P6. Optionally, switching between pumps may be performed during a single pumping session, for example, to allow time for the pumps already used to cool.

The pumps may be any type of commercially available air pump. One particular non-limiting example of a suitable pump is a diaphragm pump, which has advantages of low cost, and low running noise. By operating a plurality of such pumps in parallel, it has been found that pumping times to reach a given target pressure are significantly reduced, and higher maximum values of suction can be reached.

In cases in which the pump design inherently occludes reverse air flow when the pump is not operating, as is the case with a diaphragm pump, the pump suction ports can optionally be directly connected to a manifold associated with a suction port of the pump unit. The processing system then provides power selectively to the micro pumps which are to be operated, and the other pumps remain passive and in a sealed state. Where the pump type does not inherently maintain a reliable seal while not powered, or if it is desired to ensure continued operation of the system in case a pump fault resulted in one pump failing in a "leaky" state, an electrically actuated cut-off valve 26 may be provided for each pump to ensure isolation of the pump from the vacuum line when the pump is not in use, or if it is detected to be faulty. (The electric actuator, such as a solenoid, associated with each valve 26 has been omitted from the drawing for clarity of presentation.) Optionally, an electrically-controlled venting valve 28, typically controlled by solenoid 30, may be provided in fluid flow connection to suction port 12, for rapid vacuum release between pulses. Most preferably, a pressure sensor 32, associated with processing system 16, is deployed to measure fluid pressure at suction port 12.

Interconnection of the pumps' suction lines is typically in parallel, such that use of multiple pumps achieves an increased air flow for a given vacuum level, reaching the desired vacuum (or pressure) level more quickly, and may also achieve increased vacuum level compared to each pump individually. An additional option made possible by use of an array of micro pumps is to combine a positive pressure output of one of more micro pumps with a negative (suction) pressure produced by other pumps to create a variety of complex and/or finely-tuned pumping patterns. If pumps are combined to operate together in opposing pumping directions, a type of pump which can maintain a pressure difference bidirectionally (i.e., without employing check valves) is preferably used.

After selecting which pumps are currently to be used, processing system 16 provides the required actuating voltage to each pump. The actuating voltages are typically the same for all pumps in use. In some cases, adjustment of the effective voltage is achieved by using pulse width modulation, i.e., providing the full (maximum) actuating voltage in rapid pulses with a percentage duty cycle chosen to provide the desired output power, as is known in the art.

In certain cases, non-synchronous switching of the individual pumps and/or other non-identical actuation voltages may be used to achieve specific complex vacuum profile effects. For example, if it is desired to have vacuum (or positive pressure) pulses superimposed over a residual base-level of vacuum suction, this may be achieved by employing one pump running continuously at relatively low power while a second pump (or pumps) are actuated in a pulsed manner to generate the pulses. In another example, plural pumps may be employed together to achieve rapid vacuum increase at the beginning of each pulse to reach a target value, and then a single pump (either one of the same pumps, or a different pump) may be used in closed-loop control to maintain the desired vacuum level for a given period after the target value has been reached.

Parenthetically, although the RALPP configuration has been described herein primarily in the context of a breast pump, it will be noted that the principles of the RALPP configuration may be applied in a wide range of other suction applications, or other pumping applications, in which a pump is required to provide dynamically varying degrees of suction, or compression, or complex pressure profiles which involve both suction and positive pressure. For example, in certain cases, improved breast milk pumping effects can be achieved by employing a relatively high constant vacuum modulated by a small amplitude "ripple" of alternating (positive and negative) pressure.

As mentioned earlier, the redundancy of the RALPP configuration allows the pump unit to continue its regular operation even if one (or more) pumps malfunctions. To this end, the processing system is preferably configured to identify suspected malfunction of motors, typically by sensing anomalies in the pump's current and/or voltage during operation, effectively performing a self-test of the pumps during normal operation. Optionally, where a vacuum sensor is present, proper operation of each pump can be directly verified during use by momentarily operating each pump alone at the beginning of a pulse and verifying that the rate of suction is within normal limits. Such a self-test impacts the suction profile of a single pulse, and would not result in any noticeable impact on the overall performance of the pump as experienced by the user.

In some cases, to facilitate servicing in the event that one or more pump develops a fault, each pump 14 is implemented as a modular unit configured to be individually replaceable with a similar pump without use of tools, such as with slide-in electrical connections and a quick connector for the suction port of the pump. Alternatively, or additionally, the pumps may be retained and released by one or more readily accessible screw, bolt or other retaining configuration which can be opened and closed either without tools or by using common tools (e.g., a screwdriver or wrench) without a need for any skilled labor.

Figure 2:
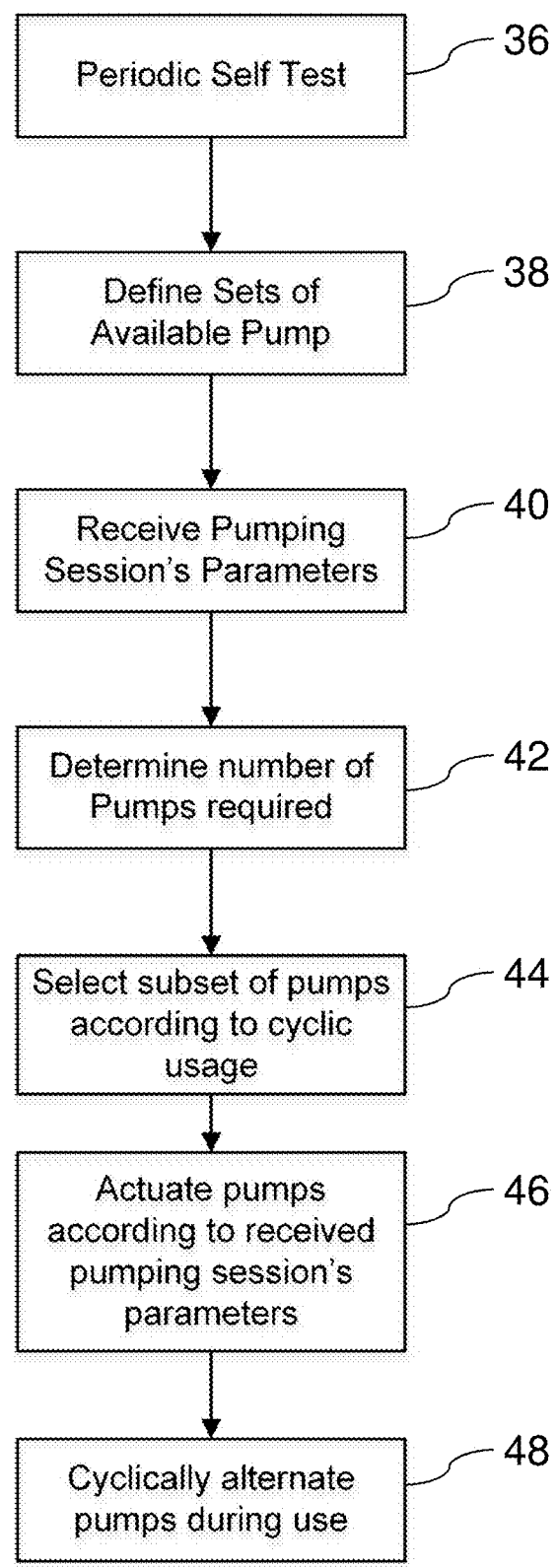
FIG. 2 is a flow diagram illustrating a mode of operation of the pump unit of FIG. 1.

Turning now to FIG. 2, this illustrates schematically a sequence of operation of suction pump unit 10, corresponding also to various aspects of a method according to the teachings of the present invention. At step 36, processing system 16 performs a periodic self-test of the pumps to identify any defective pump among said plurality of pumps 14 and, at step 38, defines the set of available pumps after excluding any defective pumps, thereby excluding the defective pump(s) from use in subsequent pumping sessions. A display of the graphic user interface 22 is preferably used to notify the user of any pumps which have malfunctioned, to prompt replacement of the faulty pumps.

At step 40, processing system 16 receives the pumping session parameters defining either the pump operation power level or the target pressure to be achieved, and typically defining a cyclic pumping pulse form, such as the forms discussed below with reference to FIGS. 3A and 3B. The session parameters may also define an overall period of the session, and optionally, two or more sequential stages of a pumping sequence, each with its own suction level and/or pulse form. The session parameters may be retrieved from storage device 20, either corresponding to the last-used parameters or selected from a number of preset or custom sets of parameters previously stored, or may be set or modified via GUI 22.

Once the desired session parameters are loaded, processing system 16 determines the number of pumps required to implement the desired session parameters (step 42), which may include different numbers of pumps operating at different stages of each pulse form, and/or during different stages of the session, and then selects which subset of the available pumps to be used (step 44), preferably taking into consideration a stored record of which pumps have recently been used in order to ensure cycling between the available pumps. The processing system then actuates the selected pumps in a suitable timed manner to implement the pumping session according to the required parameters (step 46). Cycling between the available pumps may also be performed during a single session (step 48).

Figure 3A:
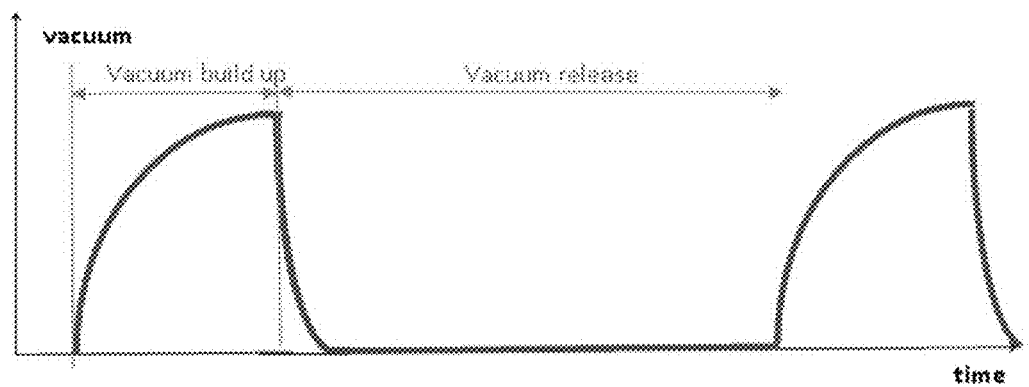
FIGS. 3A and 3B are graphs illustrating schematically two firms of cyclic suction pulse profile generated by the pump unit of FIG. 1.

FIG. 3A shows a simple exemplary pulsed cyclic suction profile which may be implemented using the suction unit 10. In this case, each pulse begins with simultaneous operation of the selected number of pumps to achieve build-up of suction to a desired level, followed by release of the vacuum, typically by opening of venting valve 28. This process is repeated to generate a sequence of similar pulses.

Suction-Hold Pulse Form

Turning now to a second aspect of the present invention, this relates to a particularly preferred suction profile generated by breast pumps according to this aspect of the present invention, and a corresponding method for operating a breast pump.

By way of introduction, referring again to FIG. 3A, the suction profile illustrated here parallels a conventional cycle called a "vacuum release cycle." In this cycle, the breast pump builds up a vacuum until it reaches a desired level and then releases this vacuum immediately after reaching the target vacuum. In this suction profile, the period for which the maximum or near-maximum vacuum is present is a small proportion of each pulse, typically no more than a few percent of the pulse length, and is an even smaller proportion of the overall cycle time.

Figure 3B:
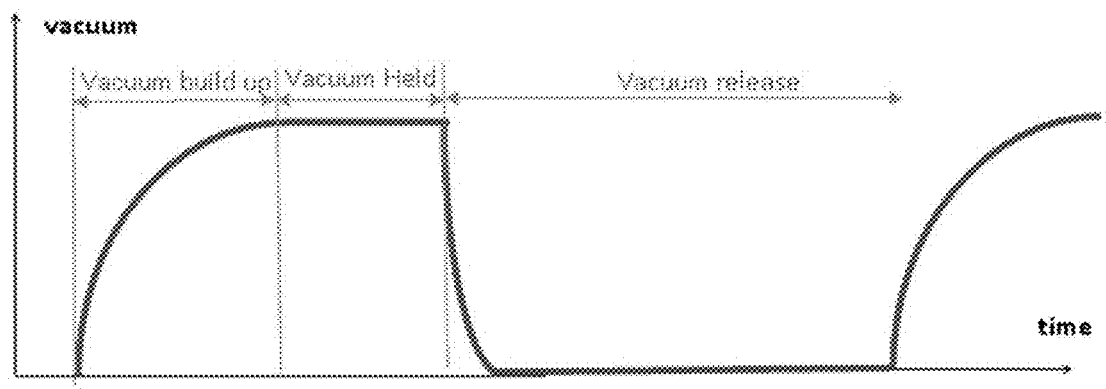

Turning now to FIG. 3B, according to this aspect of the present invention, processing system 16 is configured to actuate pumps 14 to generate a cyclic time-varying suction profile, as illustrated schematically in FIG. 3B, each cycle of the suction profile including:

(a) a suction rise ("vacuum build-up") time during which the suction increases to a target value;

(b) a suction (vacuum) hold time during which the suction is maintained substantially at said target value; and (c) a suction (vacuum) release time during which the suction is released to fall to a base value, It is a particular feature of this aspect of the present invention that the suction hold time is a significant proportion, typically in excess of 15%, of the total cycle time, and in most preferred implementations, the suction hold time is in excess of 20%, and most preferably between 25% and 40% of the entire cycle time. Additionally, the suction hold time is preferably at least 40%, and most preferably at least half, of a total pulse time, defined as the sum of the suction rise time and the suction hold time. In absolute terms, a preferable duration of the vacuum hold time is preferably at least 250 ms. The presence of a sustained vacuum hold period in the suction pulse form is believed to mimic more accurately the manner in which an infant naturally suckles, and has been found to be highly effective in extracting breast milk.

For the purpose of the above definitions, the vacuum is considered to be help "substantially constant" if it varies by less than 10% of the vacuum level (i.e., of the difference between the suction pressure and atmospheric pressure) during the "vacuum hold" period.

The vacuum hold period may be passive, in the sense that pumping is stopped, and the vacuum remains within the system, in which case slow subsiding of the vacuum level may be observed due to imperfect sealing of the connected pumping kit against the breast or elsewhere.

For the purpose of the description and claims of the present invention, such conditions are referred to as "maintaining the vacuum", and typically result in a slow decrease, preferably dropping less than 10% of the vacuum level over the "hold" period, and typically by not more than about 5%.

Alternatively, the vacuum level may be maintained actively, i.e., by use of closed-loop control in which a pressure sensor monitors the vacuum level and the processing system selectively actuates the pump to top-up the vacuum if needed. In this case, depending on the resolution of the pressure sensor and precision of the control loop and pump control, the "vacuum hold" profile may include small variations as the "top-up" occurs. These variations are preferably within 5%, and more preferably within 3%, of the desired suction level pressure, and most preferably maintain the vacuum level constant to within a margin of accuracy of ±5 mmHg.

Figure 4:
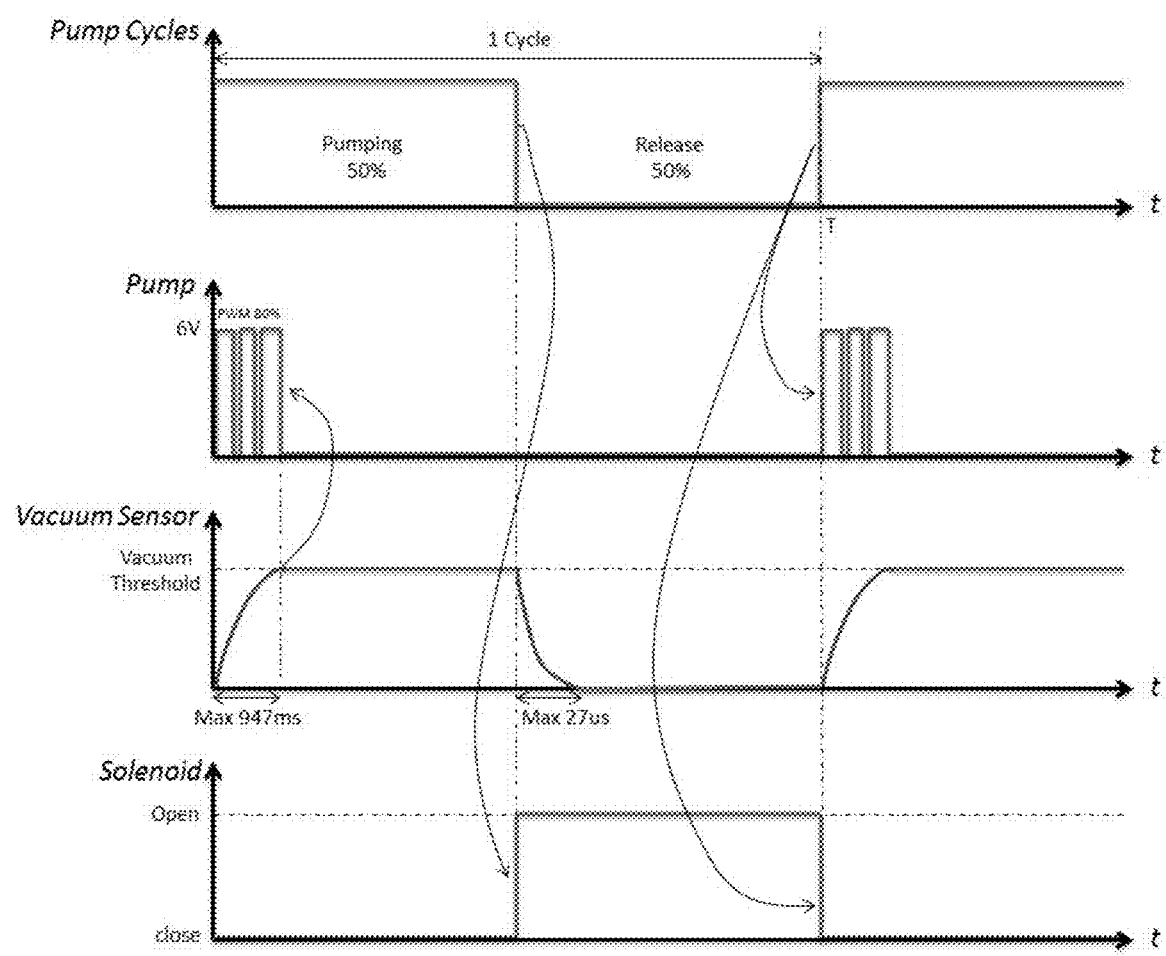
FIG. 4 is a set of graphs illustrating different aspects of the operation of the pump unit of FIG. 1 during generation of the pulse profile of FIG. 3B.

FIG. 4 is a schematic time diagram illustrating the operation time-line of a breast pump implementing this aspect of the present invention according to one non-limiting example. This non-limiting example relates to a case where a single micro pump is used with a target vacuum threshold of 250 mmHg below atmospheric pressure, and is used in connection with a pump set for single sided pumping (one breast).

In the non-limiting example of FIG. 4, each cycle of vacuum process is defined by 2 steps: a 50% pumping process including the vacuum-hold period; and a 50% pressure release period vented to atmospheric pressure, as represented in the top plot of the figure. The remaining plots, from top to bottom, represent a driving voltage applied to the suction pump in use, the output of the vacuum sensor indicating suction pressure below atmospheric pressure in the +Y direction, and the actuating voltage of solenoid 30 operating venting valve 28

In the suction profile as illustrated, the profile is made up essentially only of a rise time, defined by the pumping limitations of the system, the vacuum hold time, and a vacuum release, which may be very rapid via a release valve, or may be damped by use of a flow restriction if preferred, but is typically significantly shorter than the rise time.

The rise time depends on the required vacuum level and the pump parameters. The maximum rise time for 250 mmHg using one small pump in one example was found to be 947 ms. This time may be shortened by using more than one pump simultaneously, or where a more powerful pump is used, or when a lower degree of suction is required. The fall time from the maximum vacuum level (250 mmHg) to atmospheric pressure was roughly 27 μsec when using a dedicated solenoid-operated venting valve without any additional flow restriction.

The overall accuracy of control of the vacuum level according to certain implementations of the invention that have been tried is typically roughly ±10 mmHg in the range of 30-60 mmHg suction, and ±5 mmHg in the range of 60-250 mmHg suction.

While the suction-hold pulse form according to this aspect of the present invention can clearly be implemented effectively using the multi-pump suction unit 10 described above, it will be appreciated that the suction-hold pulse form can readily be implemented using otherwise conventional pump hardware with suitable modification of the device logic circuitry, software and/or firmware, all as will be clear to a person having ordinary skill in the art.

Pumping Kit Disconnection Sensing

Turning now to a third aspect of the present invention, this relates to features allowing a breast pump to identify and address a situation in which it is operating while not effectively coupled to a milk collection kit.

By way of introduction, during normal operation of a breast pump, the user attaches a milk collection kit (typically including a set of tubing, a breast-shield and a bottle, optionally doubled-up for simultaneous extraction from two breasts) and applies it to the breast while starting the pumping session. It is the responsibility of the user to finish the pumping session and stop the pump once the session is over. The breast pump is not "aware" whether a kit is actually connected and if there is a reason to start or stop its motor.

According to the third aspect of the present invention, the breast pump device is configured to detect whether a collection kit is currently connected to the pump unit and is being used properly. If it detects that a user has turned its motor on and yet no kit is attached, it preferably warns the user and/or, after certain amount of time that the situation persists with no kit detected attached to the pump, it stops operation of the pump motor.

Thus, according to this aspect of the invention, processing system 16 is further configured to process data derived from at least one sensor to determine during operation of the breast pump unit whether the breast pump unit is operating in a normal suction state or in an unsealed state in which the suction pump fails to achieve effective suction, and to perform a corrective action if the unsealed state persists for a given time period of operation of the breast pump unit. The corrective action preferably includes generating a visual and/or audio alert to inform the user that the device is running without achieving the expected level of suction. Additionally, or alternatively, the corrective action includes automatically discontinuing operation of the pump unit.

The invention thus saves energy, battery life and motor life when there is no practical reason to operate the motor. An indication of a failure to achieve the expected level of vacuum may also be important in helping the user identify and correct situations in which a collection kit has not been correctly assembled, or has not be properly applied to the breast.

According to a first subset of implementations, the sensor is implemented in the drive circuitry of the pump(s) 14 and detection is achieved by monitoring the electrical characteristics of the motor under varying load occurring during pumping. Specifically, under normal operating conditions with a collection set attached and correctly applied to the breast, activation of the pump motor quickly leads to a build-up of partial vacuum in the collection set and a correspondingly increased load on the motor. This increased load is reflected in an increased current drawn by the motor compared to its free-running or "idling" state. According to this subset of implementations, one or more electric sensor detects the increase in current, or some corresponding detectable variation in current or voltage across one or more component of the circuitry, and digital or analogue logic circuitry determines whether the motor load is within an expected range of values. If the motor load remains below an expected value a given time after actuation, this indicates a low-load output corresponding to a failure to achieve the expected vacuum.

According to an alternative subset of implementations, where a pressure sensor 32 is deployed to detect the pressure within at least part of the collection set, the error state can be detected directly by the failure of the system to reduce the pressure below a given threshold value for effective breast pump operation within a defined period after the start of operation of the pump.

According to either sensing mode, where the pump is operated to generate a cyclic pulsed suction profile, the sensing of below-expected motor load or suction value is clearly performed only during the relevant portion of the pulse cycle. When referring herein to persistence of the error condition for a given time period, this refers to repetitive detection of the error condition during the relevant portions of successive pulse cycles in the operation of the pump over the given time period.

If the sensed failure to generate the expected vacuum (suction) persists for a predefined amount of time (T1), a warning signal is preferably conveyed to the user. This warning signal may be an audio signal, such as a beep or a verbal spoken message, and/or may include a visual signal, such as a flashing light and/or a display indicating the problem pictorially or in words. This warning prompts the user to check proper connection of the milk collection set, and proper application of the set to the body. A typical value for T1 may be in the range of 10-20 seconds.

Additionally, or alternatively, if the non-suction state persists for longer amount of time (T2), the control logic of the pump device preferably turns off the motor to reduce power consumption and conserve battery life and motor life. A typical value for T2 may be 20-30 seconds in cases where no warning message is provided. Where a warning message is provided, a slightly longer period before shut-off may be desired to allow the user to correct the problem, in which case a value in the range of 30-60 seconds may be preferred.

In certain cases, the system may distinguish between different types of error condition and generate distinct warning messages for each condition. For example, failure to connect a collection set may result in a load similar to idling conditions and a pressure close to atmospheric pressure, while improper assembly of the kit or imperfect application to the body may result in an intermediate level of load and suction. A corresponding audio or visual warning message may then provide a corresponding indication to the user of what corrective action is recommended.

While the disconnection detection features according to this aspect of the present invention can clearly be implemented effectively using the multi-pump suction unit 10 described above, it will be appreciated that these features can also readily be implemented using otherwise conventional pump hardware with suitable modification of the device logic circuitry, software and/or firmware, all as will be clear to a person having ordinary skill in the art.

Touch Screen as Lower Switch

Turning now to a fourth aspect of the present invention, this relates to implementation of a breast pump in which a resistive touch screen serves as a power switch to switch on the unit.

By way of introduction, touch panels, and particularly touch screens (i.e., touch panels integrated with a display), have become a very popular form of user interface, controlling a wide range of device functions when the device is in its ON state and operational. Touch panels, however, are inoperative when a device is in an OFF state, powered down. As a result, touch panels are normally supplemented by a conventional mechanical switch (button or the like) for activating the device when switched OFF to turn it ON.

According to the fourth aspect of the present invention, the graphic user interface 22 is implemented using a touch panel, or touch screen, as a power switch to turn a device from OFF to ON, without requiring any separate conventional mechanical switch.

Figure 5:
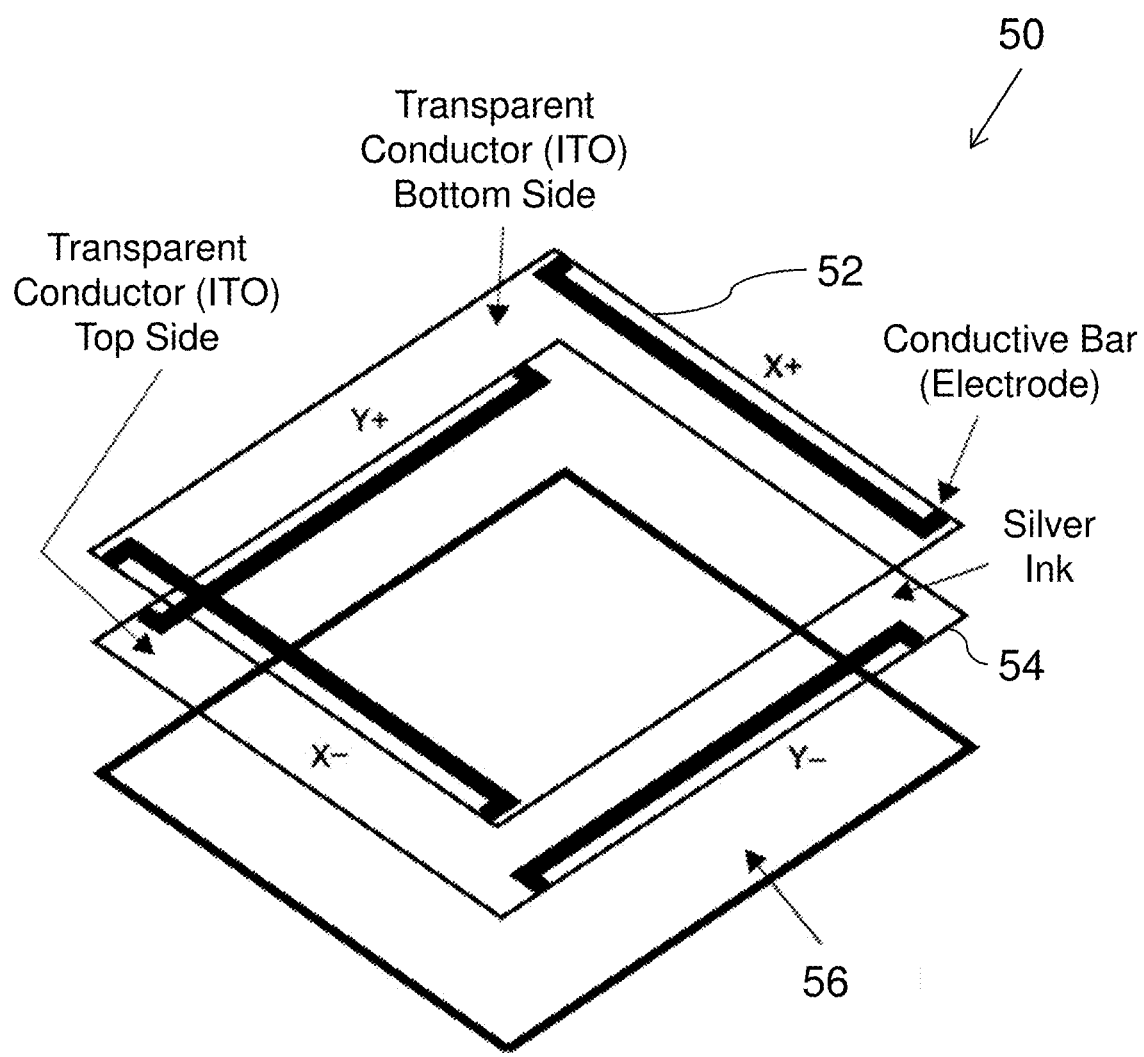
FIG. 5 is a schematic exploded isometric view of components of a touch screen panel for use in the pump unit of FIG. 1.
Figure 6:
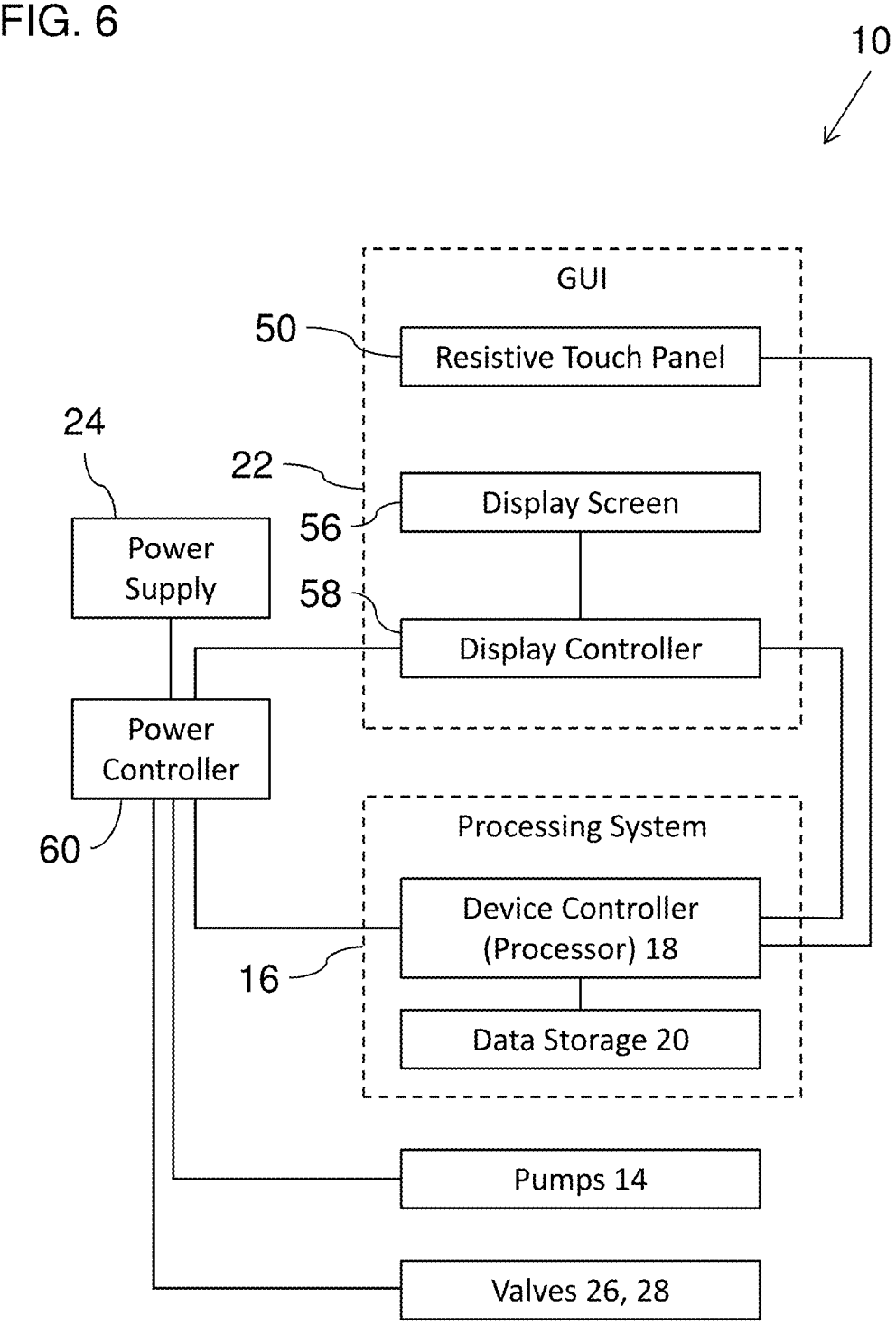
FIG. 6 is a schematic block diagram of the pump unit of FIG. 1 showing additional detail of an implementation of the invention employing a resistive touch screen.

Referring to FIG. 5, this illustrates schematically a structure of a typical resistive touch panel or screen 50, suitable for use as part of GUI 22, having a first transparent conductive layer 52 and a second transparent conductive layer 54 arranged in facing relation to first conductive layer 52 so as to be selectively brought into electrical contact with each other on application of mechanical pressure to panel 50. A display screen 56 preferably underlies the touch panel. Further components of this implementation of the present invention are illustrated in FIG. 6, including a display controller 58 for driving operation of display screen 56. Touch panel controller circuitry (here implemented as part of processing system 16 which serves also as the device controller) is provided for driving electrodes associated with at least one of conductive layers 52 and 54 during operation of the pump unit so as to generate signals sufficient to determine a screen location at which mechanical pressure is applied. The pump unit is configured to assume an off configuration in which display controller 58 is powered-down and processing system 16 is in a sleep mode with an open-circuit voltage differential applied between first and second conductive layers 52 and 54 such that the touch panel serves as a power-on switch effective to initiate awakening of processing system 16 and powering-up of display controller 58 when mechanical pressure is applied to said resistive touch panel. Switching of the power to the various components is preferably achieved by control signals sent by processing system 16 to a power controller 60 which selectively supplies power from power supply 24 to the various other components.

Optionally, the system incorporates delay circuitry, which may be either analog or digital circuitry, associated with the touch screen controller in the power-off configuration and configured to be actuated on closure of the touch panel "switch" such that pressure on the touch screen effects power-up of the system only when mechanical pressure is applied to the touch screen for a period in excess of a defined delay.

Unlike the feather-light sensitivity of capacitive touch panels, resistive touch panels require a minimum contact pressure to operate them, making them particularly suited to control of device settings where accidental changes are to be avoided. During normal operation, while the device is activated, the panel employs one of a number of known techniques for determining the location in two dimensions of applied pressure. One non-limiting example of an implementation of such a touch panel is described in an article "Using resistive touch screens for human/machine interface" by Rick Downs (Texas Instruments Inc., Analog Applications Journal, 3Q 2005, pp. 5-9). The location of contact is identified by applying a voltage between electrodes at opposite edges of one dimension of one of the conductor and identifying the contact location according to the voltage which is conveyed to the other conductor, effectively functioning as a potential divider between the two electrodes. The actuating voltage is applied alternately between electrodes in the X and Y directions to determine the touch location in two dimensions.

According to the teachings of the present invention, a distinct mode of operation of the panel is preferably introduced for use when the device is "OFF", i.e., when processing system 16 is powered down, and most preferably when the touch panel controller circuitry is also powered down. Specifically, in this example, one electrode can be raised to a fixed voltage V while the other is kept at −V or 0 (ground). This turns the panel into a simple on/off switch with a normally open configuration, in which no current flows unless or until pressure is applied to the panel (at any location), forming contact between the electrodes and allowing a current to flow. This is taken as an "ON" actuation command, after which the device is actuated to its normal "ON" state, and the touch panel starts operating according to its normal position-sensing mode.

Optionally, in order to avoid inadvertent switching on of the device, a delay circuit, or functionally similar digital circuitry, may be used to delay actuation of the device until pressure has been applied to the touch panel for a predefined minimum period, such as 1 second, or if preferred, at least 3 seconds.

Figure 7:
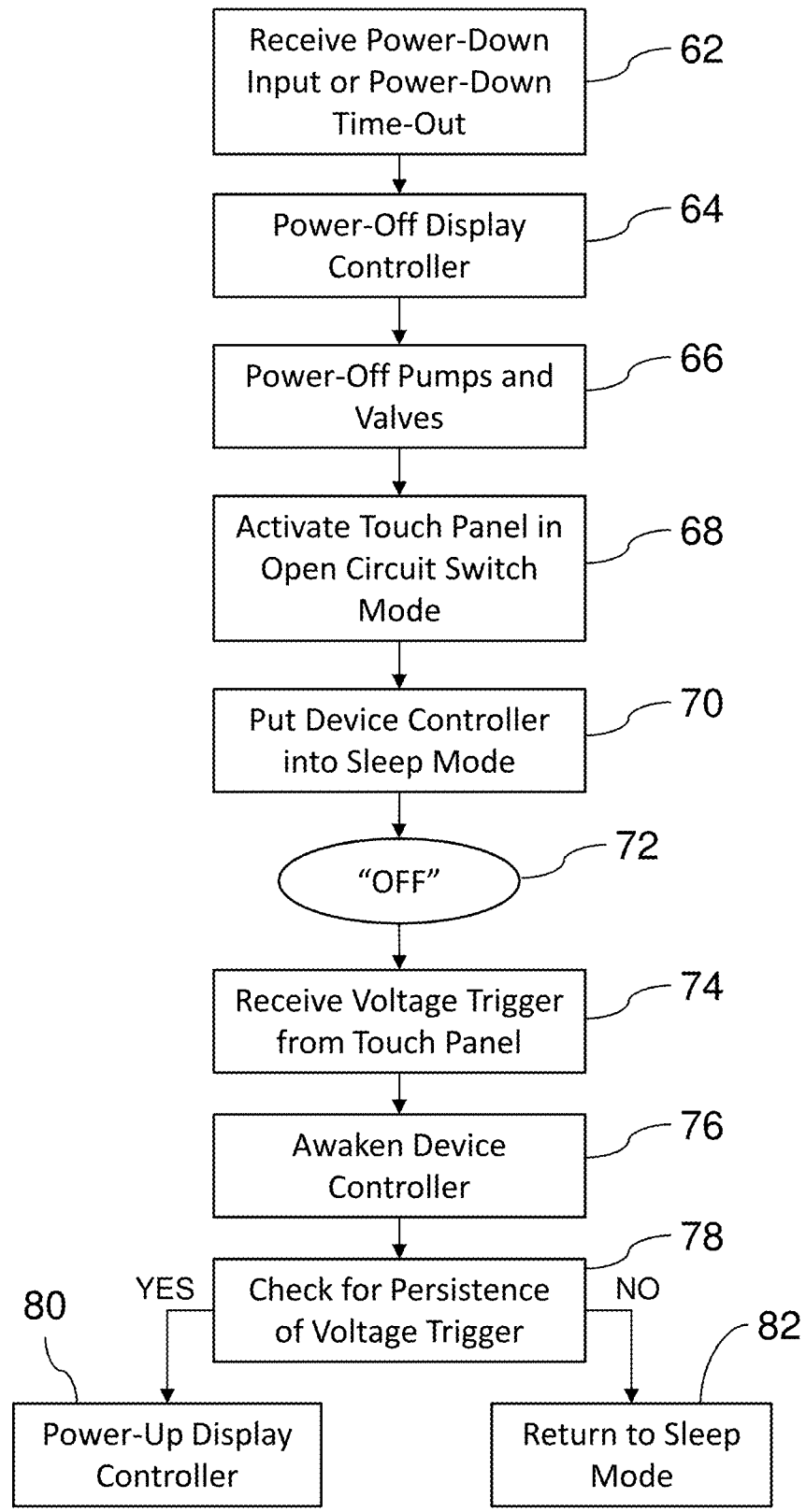
FIG. 7 is a flow diagram illustrating an implementation of a power-off and power-on cycle in the pump unit of FIG. 6.

FIG. 7 illustrates a typical cycle of power-off and power-on operations according to an implementation of this aspect of the invention according to the exemplary embodiment of FIG. 6. At step 62, the processing system receives an input indicative of a need to switch off the device. This may be in the form of a user input via GUI 22, or may be a self-generated request based on a power-down time-out, such as a period of inactivity of the device, or a period of ineffective usage as discussed above. Processing system 16 responds to the power-down request by powering-off display controller 58 and the various device components such as any pumps or valves which had been activated, typically by suitable instructions to power controller 60 (steps 64 and 66). The touch panel driving circuitry, here also implemented as part of processing system 16, then activates touch panel 50 in open circuit switch mode, with a voltage between the conductors (step 68) so that contact between the conductors will change a voltage applied to an input of the processing system so as to traverse a threshold effective to awaken the processing system from a sleep mode. The device controller then puts itself into sleep mode (step 70) and the device thereby assumes its "OFF" state (step 72).

It will be noted that the device controller of most medical devices, including pumps as described herein and a wide range of other diagnostic, therapeutic or other medical devices, are typically relatively low processing-power and low board speed processors which, in their suspended ("sleep") state typically have extremely low power consumption and can offer long periods of "sleep" status with negligible drain on a battery power supply. This is typically in contrast to a display controller, which includes circuitry to support proper operation of a display screen, which is much higher energy consumption. For this reason, this aspect of the present invention provides pronounced advantages by putting the touch-panel controller separately from the display controller, thereby allowing full power-off of the display controller while maintaining the power-on capabilities of the resistive touch screen with minimal power consumption.

While in the off state, when mechanical pressure is applied to the touch panel, this connects the two conductors and swings an input voltage to the processing system across a threshold (step 74), thereby triggering awakening of processing system 16 (step 76). Processing system 16 then checks whether this voltage trigger has persisted for more than a predefined waiting period, for example 2-3 seconds, in order to identify the pressure as an intentional "ON" signal. If the signal persists, at step 80, the display controller and any other remaining components are powered up, ready for operation of the device. If the voltage trigger is found not to persist for the defined minimum period, at step 82, the processing system returns to its sleep mode, awaiting a subsequent pressure on the touch panel.

Optionally, the persistence of the pressure on the touch panel may be verified by delay circuitry of a dedicated touch panel controller, or other dedicated circuitry provided specially for handling the "off" state, thereby avoiding the need to awaken the device controller prior to verification of the "on" signal. Additionally, or alternatively, an "on" signal may be conditional on some specific sequence of pressures applied to the touch panel such as, for example, a double tap.

The on-switch functionality of this aspect of the present invention facilitates implementations of various devices and appliances without a dedicated on/off switch, thereby potentially reducing the number of components, improving reliability, and/or facilitating the use of a larger proportion of the device surface area for the touch panel, which is particularly important in the case of a touch-panel display. This may also facilitate reduction in the dimensions of the device and/or improvement to ergonomic or aesthetic aspects of the product design by avoiding the need for an addition, separately-positioned dedicated on/off switch.

One particularly advantageous and preferred implementation of the present invention is in the context of the breast pump described herein. However, it will be clear that this aspect of the present invention is applicable to a wide range of other applications in which resistive touch panels or displays are employed.

It will be appreciated that the above descriptions are intended only to serve as examples, and that many other embodiments are possible within the scope of the present invention as defined in the appended claims.

What is claimed is:

1. A pump unit comprising:
   (a) a plurality of electrically-powered air pumps, each of said pumps having a port, said ports of all of said pumps being in fluid connection to a combined port of the pump unit;
   (b) a processing system comprising at least one processor, said processing system being connected to each of said pumps for independent actuation of each of said pumps; and
   (c) a user interface associated with said processing system for user actuation of the pump unit according to any of a plurality of required levels of suction or according to any of a plurality of required levels of pressure,
   wherein said processing system is configured to:
   (i) determine a number of said pumps that is required to generate the required level of suction or pressure; and
   (ii) to selectively actuate said number of said pumps in order to generate the required level of suction or pressure,
   and wherein said combined port of the pump unit is a suction or gas pressure port of a medical device.

2. The pump unit of claim 1, wherein, when said number of said pumps for a selected one of said plurality of required levels of pressure is less than all of said pumps, said processing system is configured to alternate between actuating at least two non-identical subsets of said pumps, said at least two subsets of said pumps generating the same level of suction or pressure at said combined port of said pump unit.

3. The pump unit of claim 1, wherein said processing system is further configured to actuate said plurality of pumps to generate a cyclic time-varying pressure profile, said processing system actuating a first number of said pumps during a first portion of each cycle of said pressure profile and a second number of pumps, different from said first number, during a second portion of each cycle of said pressure profile.

4. The pump unit of claim 1, wherein each of said pumps is provided with an electrically controlled cut-off valve, and wherein said processing system is further configured to actuate said electrically controlled cut-off valve to block flow to said combined port through at least one of said pumps that is not currently actuated.

5. The pump unit of claim 1, wherein each of said pumps is a diaphragm pump.

6. The pump unit of claim 1, wherein each of said pumps is a modular unit configured to be individually replaceable with a similar pump without use of tools.

7. The pump unit of claim 1, further comprising a pressure sensor, associated with said processing system, and deployed to measure a fluid pressure at the combined port.

8. The pump unit of claim 1, further comprising an electrically actuatable vent valve, connected so as to be controlled by said processing system, and deployed to selectively allow rapid release of suction or pressure at the combined port.

9. The pump unit of claim 1, wherein said processing system is further configured to actuate said plurality of pumps to generate a cyclic time-varying suction profile, each cycle of said suction profile including:
   (a) a suction rise time during which the suction increases to a target value;

(b) a suction hold time during which the suction is maintained substantially at said target value; and (c) a suction release time during which the suction is released to fall to a base value, wherein said suction hold time is at least 15% of a total cycle time.

10. The pump unit of claim 9, wherein said suction rise time and said suction hold time together make up a total pulse time within each cycle, and wherein said suction hold time is at least 40% of said total pulse time and at least a 20% of a total cycle time.

11. The pump unit of claim 1, wherein said processing system is further configured to process data derived from at least one sensor to determine during operation of the pump unit whether the pump is operating in a normal state or in an unsealed state in which the pump fails to achieve effective suction or pressure, and wherein said processing system is further configured to perform a corrective action if said unsealed state persists for a given time period of operation of the pump unit.

12. The pump unit of claim 11, wherein said corrective action includes generating a visual and/or audio alert.

13. The pump unit of claim 11, wherein said corrective action includes discontinuing operation of the pump unit.

14. The pump unit of claim 1, wherein said user interface comprises a resistive touch panel having a transparent first conductive layer and a transparent second conductive layer arranged in facing relation to said first conductive layer so as to be selectively brought into electrical contact with said first conductive layer on application of mechanical pressure to said resistive touch panel, a display screen underlying said touch panel, a display controller for driving said display screen, and touch panel circuitry for driving electrodes associated with at least one of said first and second conductive layers so as to generate signals sufficient to determine a panel location at which mechanical pressure is applied, wherein the pump unit is configured to assume an off configuration in which said display controller is powered-down and said processing system is in a sleep mode with an open-circuit voltage differential applied between said first and second conductive layers, said touch panel serving as a power-on switch effective to initiate awakening of said processing system and powering-up of said display controller when mechanical pressure is applied to said resistive touch panel.

15. The pump unit of claim 14, wherein said touch panel circuitry is implemented as part of said processing system.

16. The pump unit of claim 14, further comprising delay circuitry associated with said resistive touch panel and configured such that said touch panel effects power-up of said processing system only when mechanical pressure is applied to said touch panel for a period in excess of a defined delay.

17. The pump unit of claim 1, wherein the pump unit is a breast pump configured to apply suction to a breast shield set connected to said combined port.

18. The pump unit of claim 1, wherein the pump unit is a suction pump unit configured to generate suction at said combined port.

19. The pump unit of claim 1, wherein said user interface defines a maximum level of suction or a maximum level of pressure, said maximum level of suction or maximum level of pressure lying in the range from 1 kPa to 500 kPa.

20. The pump unit of claim 1, wherein said user interface defines a maximum level of suction or a maximum level of pressure, said maximum level of suction or maximum level of pressure lying in the range from 50 kPa to 200 kPa.

21. A pump unit comprising:

(a) a plurality of air pumps, each of said pumps having a port, said ports of all of said pumps being in fluid connection to a combined port of the pump unit;

(b) a processing system comprising at least one processor, said processing system being connected to each of said pumps for independent actuation of each of said pumps; and (c) a user interface associated with said processing system for user actuation of the pump unit according to any of a plurality of required levels of suction or according to any of a plurality of required levels of pressure, wherein said processing system is configured to:

(i) determine a number of said pumps that is required to generate the required level of suction or pressure;

(ii) to selectively actuate said number of said pumps in order to generate the required level of suction or pressure;

(iii) to perform a self-test to identify any defective pump among said plurality of pumps; and (iv) to selectively actuate said number of said pumps without use of said defective pump, and wherein said combined port of the pump unit is a suction or gas pressure port of a medical device.

22. A pump unit comprising:

(a) a plurality of air pumps, each of said pumps having a port, said ports of all of said pumps being in fluid connection to a combined port of the pump unit;

(b) a processing system comprising at least one processor, said processing system being connected to each of said pumps for independent actuation of each of said pumps; and (c) a user interface associated with said processing system for user actuation of the pump unit according to any of a plurality of required levels of suction or according to any of a plurality of required levels of pressure, wherein said processing system is configured to:

(i) determine a number of said pumps that is required to generate the required level of suction or pressure; and (ii) to selectively actuate said number of said pumps in order to generate the required level of suction or pressure, wherein said combined port of the pump unit is a suction or gas pressure port of a medical device, and wherein, when said number of said pumps for a selected one of said plurality of required levels of pressure is less than all of said pumps, said processing system is configured to alternate between actuating at least two non-identical subsets of said pumps, said at least two subsets of said pumps generating the same level of suction or pressure at said combined port of said pump unit.

* * * * *